(12) United States Patent
Pilon et al.

(10) Patent No.: US 7,904,140 B2
(45) Date of Patent: Mar. 8, 2011

(54) TIME-RESOLVED NON-INVASIVE OPTOMETRIC DEVICE FOR MEDICAL DIAGNOSTIC

(75) Inventors: Laurent G. Pilon, Los Angeles, CA (US); Kamal M. Katika, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 801 days.

(21) Appl. No.: 11/610,430

(22) Filed: Dec. 13, 2006

(65) Prior Publication Data

US 2007/0156037 A1    Jul. 5, 2007

Related U.S. Application Data

(63) Continuation of application No. PCT/US2005/021594, filed on Jun. 17, 2005.

(60) Provisional application No. 60/581,151, filed on Jun. 17, 2004.

(51) Int. Cl.
*A61B 6/00* (2006.01)

(52) U.S. Cl. ........................................ 600/476

(58) Field of Classification Search .................. 600/476
See application file for complete search history.

(56) References Cited

U.S. PATENT DOCUMENTS

| 5,222,496 | A | * | 6/1993 | Clarke et al. .................. 600/316 |
| 5,424,841 | A | * | 6/1995 | Van Gelder et al. .......... 356/417 |
| 5,448,992 | A | | 9/1995 | Kupershmidt |
| 5,517,987 | A | * | 5/1996 | Tsuchiya ...................... 600/328 |
| 5,572,996 | A | | 11/1996 | Doiron et al. |
| 5,676,140 | A | | 10/1997 | Ukawa et al. |
| 5,909,278 | A | * | 6/1999 | Deka et al. .................... 356/318 |
| 5,933,792 | A | * | 8/1999 | Andersen et al. .............. 702/32 |
| 6,020,126 | A | * | 2/2000 | Carlsson et al. ................. 435/6 |
| 6,066,459 | A | * | 5/2000 | Garini et al. ..................... 435/6 |
| 6,319,540 | B1 | | 11/2001 | Van Antwerp et al. |

(Continued)

FOREIGN PATENT DOCUMENTS

WO        00/14515 A1     3/2000

(Continued)

OTHER PUBLICATIONS

Adaptive modified method of characteristics to solve the one-dimensional solute transport equation, Liu, Hui Hai, Dane, J H, Guven, O. Soil Science Society of America Journal. Madison: May 1995. vol. 59, Iss. 3; p. 677.*

(Continued)

*Primary Examiner* — Long V Le
*Assistant Examiner* — Saurel J Selkin
(74) *Attorney, Agent, or Firm* — John P. O'Banion

(57) ABSTRACT

A time-resolved fluorescence device is described for the detection and diagnosis of various metabolic diseases in a noninvasive or minimally invasive manner. The device uses an ultra-short excitation pulse that comprises of a repetition of nanosecond pulses. The excitation pulse is directed incident onto a strategically selected area of the patient body such as the forearm, the feet, and the palm. This light interacts with the different layers of the skin. The absorbed light excites conditions of interest in the skin, which in turn generate a fluorescence signal, which is collected by a detector. A processor is coupled to the detector to measure the transient fluorescence intensity decay of the skin in terms of lifetimes, and the contribution of individual fluorophores to the overall fluorescence signal.

23 Claims, 9 Drawing Sheets

U.S. PATENT DOCUMENTS

| | | | |
|---|---|---|---|
| 6,567,678 B1 * | 5/2003 | Oosta et al. | 600/316 |
| 6,584,342 B1 | 6/2003 | Trushin et al. | |
| 6,675,030 B2 * | 1/2004 | Ciurczak et al. | 600/316 |
| 6,721,582 B2 | 4/2004 | Trepagnier et al. | |
| 6,728,560 B2 * | 4/2004 | Kollias et al. | 600/316 |
| 6,740,890 B1 * | 5/2004 | Tai | 250/458.1 |
| 6,801,798 B2 * | 10/2004 | Geddes et al. | 600/323 |
| 2002/0016534 A1 * | 2/2002 | Trepagnier et al. | 600/316 |
| 2002/0082487 A1 * | 6/2002 | Kollias et al. | 600/316 |
| 2002/0101586 A1 * | 8/2002 | Kim et al. | 356/319 |
| 2002/0158211 A1 * | 10/2002 | Gillispie | 250/458.1 |
| 2002/0193672 A1 | 12/2002 | Walsh et al. | |
| 2003/0165428 A1 * | 9/2003 | McCombs | 424/9.2 |
| 2003/0228682 A1 * | 12/2003 | Lakowicz et al. | 435/287.2 |
| 2005/0031536 A1 * | 2/2005 | Gryczynski et al. | 424/9.1 |
| 2005/0148834 A1 | 7/2005 | Hull et al. | |
| 2008/0096281 A1 * | 4/2008 | Geddes et al. | 436/63 |

FOREIGN PATENT DOCUMENTS

| | | |
|---|---|---|
| WO | 01/22869 A1 | 4/2001 |

OTHER PUBLICATIONS

Lorenzo Brancaleon et al. "In vivo fluorescence spectroscopy of nonmelanoma skin cancer", Photochemistry and Photobiology, vol. 73, No. 2, pp. 178-183 (2001).

R. Meerwaldt et al. "Simple non-invasive assessment of advanced glycation endproduct accumulation", Diabetologia, vol. 47, pp. 1324-1330, published online Jul. 9, 2004.

Konig, K. et al. High resolution multiphoton tomography of human skin with subcellular spatial resolution and picosecond time resolution. J. Biomedical Optics, Jul. 2003, vol. 8, No. 3, pp. 432-439.

Brown, C. et al. Clinical assessment of near-infrared spectroscopy for noninvasive diabetes screening. Diabetes Technology and Therapeutics, vol. 7, pp. 456-466, 2005.

Hull, E. et al. Noninvasive optical detection of diabetes: model studies with porcine skin. Optics Express, vol. 12, pp. 4496-4510, 2004.

Meerwaldt, R. et al. Increased skin autofluorescence in diabetes mellitus and renal failure. Diabetologia, vol. 44 (Supp.), p. A1046, 2000. (abstract only).

Meerwaldt, R. et al. Simple non-invasive assessment of advanced glycation endproduct accumulation. Diabetologia, vol. 47, pp. 1324-1330, 2004.

Meerwaldt, R. et al. Increased accumulation of skin advanced glycation end-products precedes and correlates with clinical manifestation of diabetic neuropathy. Diabetologia, vol. 48, pp. 1637-1644, 2005.

Mulder, D.J. et al. Skin autofluorescence, a novel marker for glycemic and oxidative stress-derived advanced glycation endproducts: an overview of current clinical studies, evidence, and limitations. Diabetes Technology & Therapeutics, vol. 8, pp. 523-525, 2006.

* cited by examiner

Incident UV excitation

Anticipated fluorescence

Incident light reaches skin surface

TIME-RESOLVED NON-INVASIVE OPTOMETRIC DEVICE FOR MEDICAL DIAGNOSTIC

CROSS-REFERENCE TO RELATED APPLICATIONS

This application claims priority from, and is a 35 U.S.C. §111(a) continuation of, co-pending PCT international application serial number PCT/US2005/021594, filed on Jun. 17, 2005, incorporated herein by reference in its entirety, which claims priority from U.S. provisional application Ser. No. 60/581,151, filed on Jun. 17, 2004, herein incorporated by reference in its entirety.

This application is related to PCT International Publication Number WO/2006/009910 A2, herein incorporated by reference in its entirety, and to PCT International Publication Number WO/2006/009906 A2, herein incorporated by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally non-invasively probing the inner structure of the skin of a patient, and more particularly to probing the inner structure of the skin of a patient through time-resolved fluorescence.

2. Description of Related Art

Fluorescence is the physical phenomenon in which light is emitted by a substance as a result of excited electrons returning to their ground states after absorption of excitation light. Substances that emit fluorescence (fluorophores) are characterized by their quantum yield, their fluorescence lifetime(s), and their emission wavelengths. Emission takes place over a spectral range and at wavelengths larger than the excitation wavelength. The quantum yield is the ratio of the number of photons emitted to the number absorbed while the fluorescence lifetime is the average time the electrons spend in their excited states. Biological tissues contain several endogenous fluorophores such as NADH, aromatic amino acids like tryptophan and structural proteins such as collagen and elastin. The optical properties of these fluorophores are sensitive to the environment and the metabolic status of the tissue making fluorescence spectroscopy a valuable tool to study the health of biological tissues.

Practically, fluorescence spectroscopy techniques consist of exposing the medium or tissue of interest to excitation light (typically UV) and measuring the fluorescence emission spectrum. The incident excitation can be a continuous or an ultra-short pulse beam of light. It can also be collimated or diffuse whether a laser or an arc-lamp is used. These measurements can be carried out in (i) a monochromatic or spectral and (ii) steady-state or time-resolved manner. Spectral measurements typically involve either emission spectral measurements or excitation spectra measurements. Fluorescence emission spectrum measurements consist of measuring the fluorescence intensity over a range of wavelengths for affixed excitation wavelength. On the contrary, excitation spectra measurements consist of measuring the fluorescence intensity at a particular wavelength for a range of excitation wavelengths.

Fluorescence of skin has been proposed as a means of diagnosing pathologic tissue by analysis of observed fluorescence spectra. Researchers have shown the feasibility of using the fluorescence spectra of skin as a means of detection of cancer of the skin. It has also been demonstrated that fluorescence can be used to distinguish fibrous plaque from healthy arterial wall. (Sterenborg H. J. C. M., Motamedi M, Wagner R. F., Thomsen S. L., Jacques S. L., 1994, *In Vivo fluorescence Spectroscopy for the diagnosis of skin diseases*, "SPIE Proceedings of Optical Biopsy and Fluorescence Spectroscopy and Imaging, edited by R. Cubeddu, R. Marchesini S. pp. 32-38.)

Recently, time-resolved fluorescence measurements have been used to identify malignant tissue (Das B. B., Feng L. and Alfano R. R, 1997, *Time-resolved fluorescence and photon migration studies in biomedical and model random media*, Reports on Progress in Physics, Vol. 60, No. 2, pp. 227-292).

They showed that time resolved fluorescence measurements can be used to distinguish malignant tumors from non malignant breast tumors. Researchers have recently shown that fluorescence lifetime measurements are generally more robust to scattering artifacts than are measurements of fluorescence spectra, even though they are sensitive to the source detector separation.

Very recently, a steady-state autofluorescence reading device was developed for assessing the accumulation of advanced glycation end products in skin (Meerwaldt, R., R. Graaff, P. H. N. Oomen, T. P. Links, J. J. Jager, N. L. Alderson, S. R. Thorpe, J. W. Baynes, R. 0. B. Gans, A. J. Smit1, 2004. *Simple non-invasive assessment of advanced glycation end-product, accumulation*, Diabetologia, Vol. 47, pp. 1324-1330). The fluorescence signal was found to correlate with the presence of several key AGEs in the skin, as well as with diabetes duration, mean HbA1C of the previous year, and creatinine levels. However, the vast majority of the human subjects were Caucasian, and measurements were performed only on the patient's forearm. Moreover, steady-state fluorescence techniques of the above device have several disadvantages that limit their effectiveness: 1) they cannot distinguish fluorophores emitting at similar wavelengths; 2) they are influenced by endogeneous chromophores, which interact with the excitation and fluorescent light; and 3) the fluorescence signal depends on the geometry and the probe design, and the properties of the skin such as pigmentation.

Various methods have been developed to simulate transient radiation transport in absorbing and scattering media. The Monte-Carlo method is often used to simulate such problems because of its simplicity, the ease by which it can be applied to arbitrary configurations and its ability to capture real physical conditions. However, it has inherent statistical errors due to its stochastic nature. It is also computationally time consuming and demands a lot of computer memory as the histories of the photons have to be stored at every instant of time. Thus, the Monte-Carlo method is ruled out in practical utilizations such as real time clinical diagnostics where computational efficiency and accuracy are major concerns.

The backward or reverse Monte Carlo has been developed as an alternative approach when solutions are needed at particular locations and times. The method is similar to the traditional Monte Carlo method, except that the photons are tracked from the detector back to the source rather than from the source to the detector as in the conventional Monte Carlo method.

There is no need to keep track of photons which do not reach the detector and so the reverse Monte Carlo method is much faster than the traditional Monte Carlo method. The method was successfully applied by (Lu X. and Hsu P.-F., Reverse Monte Carlo method for transient radiative transfer in participating media, Proceedings of the ASME International Mechanical Engineering Congress and Exposition, 2003) to simulate transient radiative transport in a non-emitting, absorbing, and anisotropically scattering one-UC dimensional slab subjected to ultra-short light pulse irradiation. But again, it has the same disadvantages as the Monte Carlo method: (i) it carries statistical errors and (ii) to solve coupled problems, it is hard to couple with other numerical schemes such as finite volume methods.

The diffusion approximation has been extensively used in biomedical applications in order to simplify light transport in biological tissues as it is simpler to solve than Equation (1). However, its validity for transient light transport in highly scattering media such as biological tissues has been questioned. Indeed, (Elaloufi, R., Carminati, R., and Greffet, J. J., 2002. *Time-dependent transport through scattering media: from radiative transfer to diffusion*, Journal of Optics A: Pure and Applied Optics, vol. 4, no. 5, pp. S103-S108) have shown that the diffusion approximation fails to describe both short-time and long-time radiation transport in thin slabs for both weakly and strongly absorbing cases. In the case of thick slabs, the diffusion approximation fails for short times. The authors have also shown that the diffusion theory always fails to predict the long-time behavior of transmitted pulses in thin slabs whose optical depth defined by $\tau_L = \sigma_S(1-g)L$ is less than eight. Researchers have examined various transport models for the simulation of ultra short laser pulses in turbide media (Kumar S. and Mitra K., 1999, *Development and Comparison of Models for Light-Pulse Transport Through Scattering Absorbing Media*, Applied Optics, Vol. 38 No. 1 pp. 188-196). They showed that there is a large difference in the temporal shape of the pulses based on the model chosen. Thus model selection would play a great role if experimentally measured temporal signals are used obtain the transport properties of the media.

Accordingly, an object of the present invention is to provide a time-resolved photometric device and the associated analysis software for detection and diagnoses of various medical conditions in a non-invasive, reliable, cheap, and convenient manner.

BRIEF SUMMARY OF THE INVENTION

A time-resolved fluorescence device is described for the detection and diagnosis of diseases in a noninvasive manner. The device uses an excitation pulse of electromagnetic (EM) wave (such as UV, IR or visible light) that comprises of a repetition of pulses (time resolution) as opposed to shining the excitation light on the patient's skin continuously (steady state). The pulse width is selected in such a way that it is much smaller than the fluorescence lifetime of the molecules or protein of interest. The excitation pulse is directed incident onto a strategically selected area of the patient body such as the forearm, the feet, the earlobes and the palm. The pulse of excitation light is partially absorbed and scattered by the different skin layers. The absorbed light excites some proteins and the AGEs in the skin which in turn generate a fluorescence signal, which is collected by a receiving detector, converted to an electrical signal, and then analyzed. A processing unit analyzes the transient fluorescence signal (e.g. intensity decay or other value) of the skin in terms of lifetimes, quantum yields, and/or the fraction of individual fluorophores contribution to the overall fluorescence signal.

The device can also monitor simultaneously the reflected and transmitted light intensity as a complementary and alternative approach. The temporal signals are then preferably processed using an inverse method developed based on transient propagation of light in multilayer biological tissues. The signal generated by the methods of the present invention is strong enough and sensitive enough to detect the fluorescence emission from proteins in the skin indicative of a diseased tissue or of a metabolic disorder.

Time resolved fluorescence techniques include but are not limited to Time-Correlated Single Photon Counting (TC-SPC), or frequency modulation, or gated photon counter. Design parameters include, but are not limited to, the energy, excitation pulse width, wavelengths of the excitation light and of the detection as well as repetition rate, detector settings, modulation frequency, gate width, etc. The areas of the body ideally suited to be probed include but are not limited to the forearms, the palms, the feet, the earlobes, and the skin flap between the thumb and the forefinger. The method of the present invention enables the determination of the type, location, and relative concentration of the fluorophores. Based on the above data, medical diagnostic may then be performed. The device and software of the present invention are small and portable allowing for earlier and regular prescreening for diabetes. In addition, it can also be applied to other diseases affecting the optical properties of skin.

The time-resolved system of the present invention eliminates many of the limitations of currently available (steady-state) systems. In particular, because different fluorophores have different lifetimes, they can be identified and their location in the skin can be determined by processing the temporal signals. Finally, the time-resolved measurements are not as sensitive to the variations in the condition of the skin (e.g., motion artifacts, pigmentation, hair, and suntan) as the steady-state method.

One aspect of the invention is a method for non-invasively probing the inner structure of the skin of a patient. The method comprises: directing an excitation pulse at a region of the patient's skin; exciting a portion of the patient's skin as a result of the excitation pulse at the region to generate a fluorescence signal indicative of the composition of the patient's skin; detecting the fluorescence signal generated by the excitation pulse; and measuring the fluorescence signal (such as intensity decay) as a function of time to detect development of a metabolic disease affecting the patient. Directing an excitation pulse generally comprises repeatedly directing a plurality of excitation pulses (e.g. ultra-short UV or near IR pulses) in succession at the region of the patient's skin.

In one embodiment, the modified method of characteristics is applied to calculate fluorescence transport within the patient's skin.

In another embodiment, the method further comprises measuring the reflectance or transmittance of the excitation pulse. Furthermore, the transmittance, reflectance, and time-resolved fluorescence measurements may be performed simultaneously.

In another embodiment of the current aspect, the method includes storing fluorescence signal values acquired from a plurality of reference patients in a database. Then the measured fluorescence signal may be compared to the stored fluorescence signal (e.g. intensity decay) values.

In yet another embodiment, the transmittance, reflectance, and time-resolved fluorescence measurements are calculated using to the modified method of characteristics. In such case, the transmittance, reflectance, and time-resolved fluorescence measurements are calculated by approximating photon paths from the detector to the source of the photons.

In some embodiments, the compared fluorescence signal may be used to monitor the long-term effect of cholesterol in the patient, or genetic changes in the patient.

In one mode of the current aspect, the method may further include identifying one or more fluorophores from the measured fluorescence signal.

One or more fluorophores may also be located within the region of skin. In a preferred embodiment, the fluorescence signal is deconvoluted to isolate the contribution of individual fluorophores to a cumulative signal.

Another aspect of the invention is an apparatus for non-invasively probing the inner structure of the skin of a patient. The apparatus has an excitation source (e.g. UV or IR LED) configured to direct excitation energy at a region of the patient's skin, and a first detector element directed at the region of skin. The first detector element is configured to receive a fluorescence signal resulting from the excitation energy at the patient's skin. The apparatus further includes a second detector element configured to receive a transmittance signal resulting from the excitation energy at the patient's skin, and a processor configured to measure fluorescence signal of the fluorescence signal as a function of time. The first detector element may also be configured to receive a transmittance signal resulting from the excitation energy at the patient's skin In one embodiment, the apparatus further comprises one or more light guides for directing the excitation energy at the region of the patient's skin, wherein the first detector element is substantially adjacent to the excitation light guides. In some cases, the second detector element is positioned substantially on an opposite the region of skin from the excitation light guides. The first and second detector elements may comprise one or more light guides for directing the fluorescence signal resulting from the excitation energy to a detector. Alternatively, the excitation source and detectors may be positioned directly adjacent to the patient's skin.

In one embodiment of the current aspect, the apparatus further comprises a monochromator to separate the reflectance signal from the fluorescence signal.

In an alternative configuration, the first detector element comprises an array of spaced apart light guides for directing a plurality of fluorescence signals resulting from the excitation energy traveling through different paths in the patient's skin to the detector. The spaced apart light guides may also be at different angles with respect to each other. The first detector element may also be oriented at different angles with respect to the excitation light guides.

Furthermore, the second detector element may include an array of spaced apart light guides for directing a plurality of fluorescence signals resulting from the excitation energy traveling through different paths in the patient's skin to the detector. In addition, the spaced apart light guides may be at different angles with respect to each other. Alternatively, the second detector element may comprise a CCD array. The second detector element may also be oriented at different angles with respect to the excitation light guides.

In an alternative embodiment, the excitation source is coupled with a sphygmomanometer cuff of a blood pressure monitoring device such that excitation energy may be directed while pressure is being applied to the region of the patient's skin.

In another aspect, blood pressure monitoring device is disclosed having a sphygmomanometer cuff, a manometer coupled to the cuff for indicating a patient's blood pressure, and an excitation source coupled to the sphygmomanometer cuff and configured to direct excitation energy at a region of the patient's skin. The device further comprises a detector directed at the region of skin and configured to receive a fluorescence signal resulting from the excitation energy at the patient's skin. Furthermore, the device may also have a processor configured to measure intensity decay of the fluorescence signal as a function of time.

In a preferred embodiment, the device is configured to simultaneously measure the patient's blood pressure and measure the intensity decay of the fluorescence signal as a function of time.

In yet another aspect, a method is disclosed for performing time-resolved fluorescence measurements on a patient. The method comprises: directing an excitation pulse at a region of the patient's skin; exciting a portion of the patient's skin as a result of the excitation pulse at the region to generate a fluorescence signal indicative of the composition of the patient's skin; detecting the fluorescence signal generated by the excitation pulse; and measuring a transient intensity decay of the fluorescence signal.

In one embodiment, a plurality of components in the patient's skin are excited, each of the components fluorescing into photons to generate the fluorescence signal. The plurality of components may be distinguished by measuring their fluorescence emission and reflectance wavelengths. Furthermore, a plurality of components having similar wavelengths may be distinguished by measuring their fluorescence lifetimes. The location of the plurality of components may be also be determined by identifying their emission and reflectance wavelengths In a preferred embodiment, the transient intensity decay measurements are calculated using to the modified method of characteristics.

In a further aspect, a method is disclosed for non-invasively probing the inner structure of the skin of a patient. The method comprises: introducing an agent into a region of the patient's skin; the agent comprising an exogenous fluorophore configured to bond to target component in the patient's skin; directing an excitation pulse at the region of the patient's skin; exciting a portion of the patient's skin as a result of the excitation pulse at the region to generate a fluorescence signal indicative of the composition of the patient's skin; the fluorescence signal comprising both exogenous fluorophores from the introduced agent and endogenous fluorophores naturally present in the patient's skin; detecting the fluorescence signal generated by the excitation pulse; and measuring a transient intensity decay of the fluorescence signal to detect development of a metabolic disease affecting the patient. The agent may be introduced via a rubbing cream having the agent placed at the region of the patient's skin.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 1 through FIG. 15. It will be appreciated that the apparatus may vary as to configuration and as to details of the parts, and that the method may vary as to the specific steps and sequence, without departing from the basic concepts as disclosed herein.

Many health conditions affect the morphology, physiology, and fluorescence characteristics of the human skin. Therefore, light transport, and in particular transient light transport and time-resolved fluorescence within the skin, differ from healthy subjects to patients with targeted disorders.

For example, presence of diabetes mellitus is generally associated with measurably thickened skin and yellow hue among diabetic patients compared with their non-diabetic counterparts. In addition to pre-diagnostic of diabetes, time-resolved fluorescence spectroscopy of skin coupled with an inverse method can be used for: monitoring acne condition in humans; studying hyper-pigmentation diagnosis of non-melanoma skin cancer; studying photo-aging caused by UV irradiation; monitoring the state of utriculus; differentiating of pre-cancer from benign conditions and from cancer; and determining the size and depth of the tumor or other anomaly. It is appreciated that the above list is not exhaustive and the proposed method may be applied to diagnose any diseases or conditions affecting the optical properties and fluorescence of the skin.

Time-resolved measurements involve measuring the lifetime of the fluorophores. To do so, the sample of interest is exposed to a pulse of light and the intensity decay is recorded using a high-speed detection system. The advantage of time-resolved over steady-state measurements is that they provide more information on the shape, flexibility and conformation state of the fluorescing molecules. This enables identification of different conformations of a molecule which would not otherwise be possible using steady-state measurements.

Figure 1:
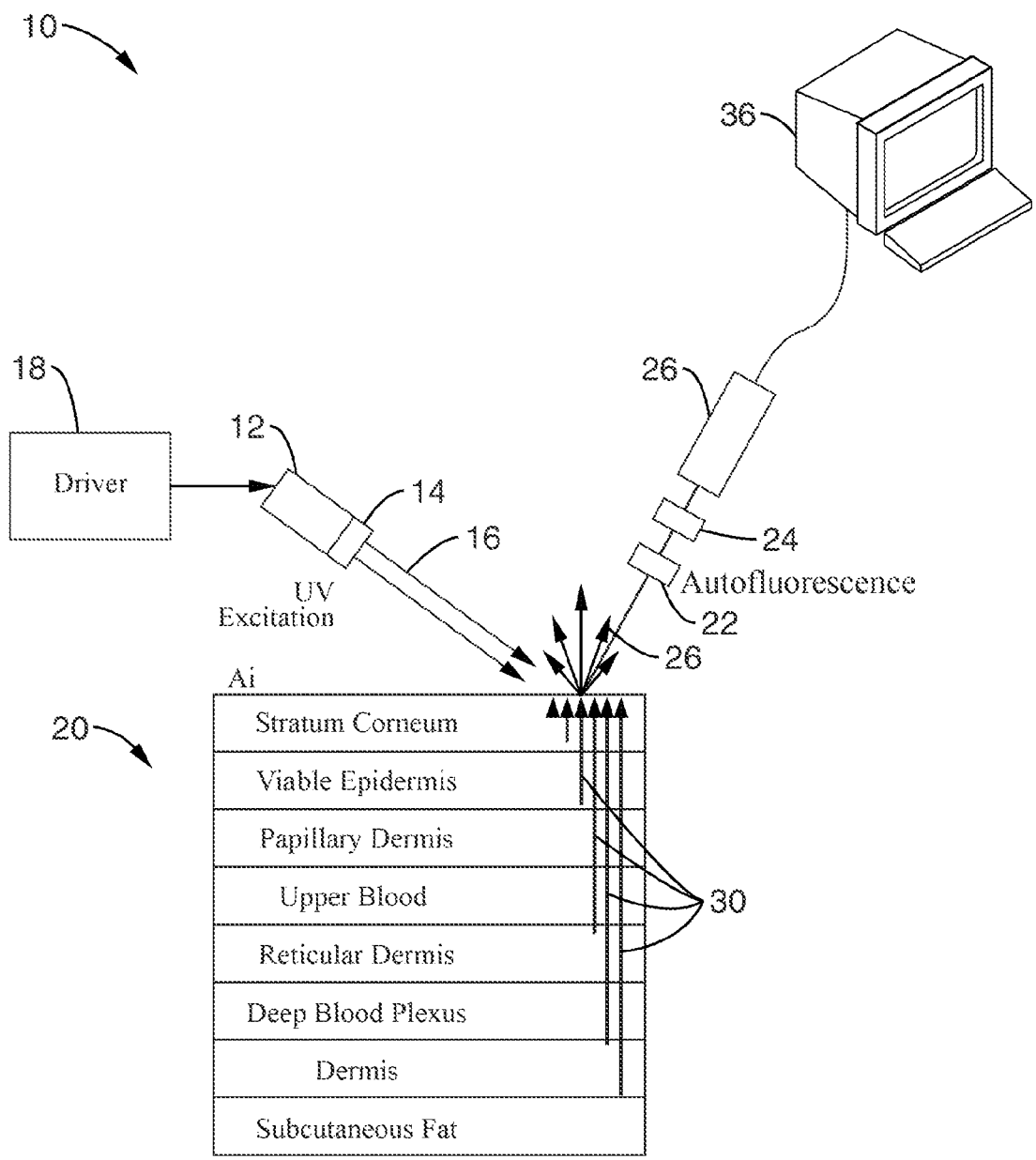
FIG. 1 is a time-resolved fluorescence optometric device in accordance with the present invention.
Figure 2:
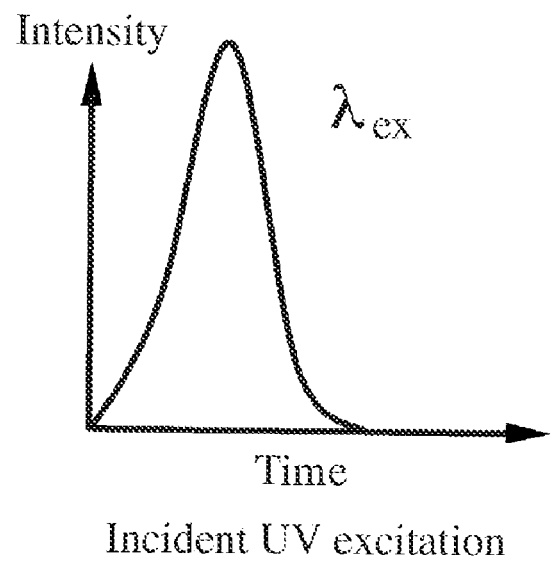
FIG. 2 is a graph of an exemplary excitation pulse over time.

Referring now to FIG. 1, an optometric device 10 for non-invasively probing the inner structure of skin is schematically described in accordance with the present invention. The optometric device 10 comprises an excitation source 12 coupled to a first light guide 14, such as fiber optic unit, to direct and transport excitation light pulses 16 to the skin 20 of a strategically selected area of the body. FIG. 2 illustrates the typical curve for incident excitation pulse intensity over time. Excitation source 12 is controlled by driver unit 18, and preferably comprises one or more pulsed sources of excitation electromagnetic (EM) waves, such as pulsed laser diodes or a pulsed light emitting diode (LED), a pulsed flash lamp, or similar device commonly used in the art. The fluorescent signal 26 is collected and transported by a second light guide 22 from the patient's skin 20 to a detector 28. It is appreciated that the excitation source 12 and detector 28 may be positioned to directly transmit and receive the signal to and from the patient's skin 20, thus the use of light guides 14, 22 are optional components of device 10, and may be removed to simplify the design.

The detector 28 may comprise a photomultiplier tube (PMT) using time correlated single photon counting, gated CCD spectrometer, streak cameras, single photon avalanche photo diode (SPAD) or similar device known in the art. In embodiments where the detector 28 comprises a PMT, a number of light guides 22 (each corresponding to an individual PMT) can be positioned in an array to measure light at different positions and light paths through the patient's skin. Alternatively, a CCD spectrometer may be used without light guides 22, the CCD having an array of pixels that allows for imaging across a two dimensional area.

Since the reflected and fluorescent signals have different wavelengths, one or more optical filters or a device separating EM waves of different wavelengths 24, such as a monochromator, may be placed in line with the second light guide 22 and the detector 28 to separate the different signals. The detector 28 and driver unit 18 are synchronized by the processing unit 36.

Figure 3:
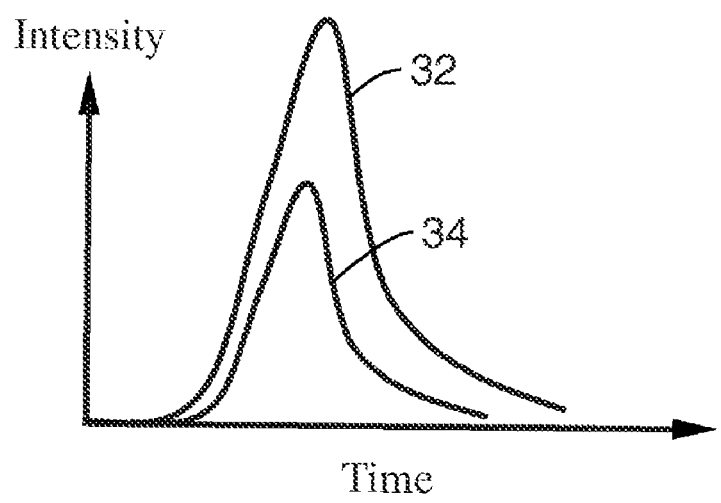
FIG. 3 is a graph comparing the fluorescence magnitude of a healthy and diabetic patient over time.

The pulse of excitation light 16 is partially absorbed and scattered by the different skin layers 20. The absorbed light excites one or more fluorophores in the skin which in turn fluoresce 30. As shown in FIG. 3, the fluorescence curve 32 for a diabetic patient differs from the curve 34 for a healthy patient. For the same subject, the curve changes also with the patient's age and health. Abnormal changes will be indicative of a change in the subject's metabolism including but not limited to impaired glucose tolerance (IGT) or diabetes. The excitation pulses may be repeatedly applied to the skin at an arbitrary rate or frequency. The successive signal is preferably added, thus increasing the signal to noise ratio and the overall quality and reliability of the detected signals.

Skin is a multi-layered structure with irregular interfaces and layers having anisotropic optical properties. There are several chromophores in the skin which absorb light. The most dominant chromophores are melanin and hemoglobin both of which absorb light in the UV (330-400 nm) and the visible (400-700 nm) part of the spectrum. In general, absorption by proteins becomes dominant at shorter wavelengths (280-330 nm). Some chromophores present in the skin also fluoresce when exposed to UV light including porphyrins, NAD/NADH, tryptophan, collagen cross links, elastin crosslinks, and keratin. Other excitation wavelengths in the visible or infrared range are also possible depending on the fluorophores and disease to be detected.

In addition to the endogenous fluorophores described above, there are a number of target cells in the body that do not naturally fluoresce by themselves. In one embodiment of the invention, fluorescence may be induced in certain target cells by introduction of exogenous fluorophores (e.g. fluorescing molecules, or nanoparticles). This may be accomplished by application of a cream onto the patient's skin (e.g. via a transdermal patch or the like) having exogenous fluorophores that bond to proteins or molecules of interest that otherwise would not fluoresce. Alternatively, delivery of the exogenous may be accomplished through a localized injection.

In another embodiment of the invention, the time-dependent reflected and fluorescence signals can be enhanced using index of refraction) matching cream. This will limit the internal reflection within the skin. A photon that reaches the air-skin interface at an angle greater than the critical angle $\theta_c$, defined by:

$$\theta_c = \arcsin(1/n_{Skin})$$

where $n_{Skin}$ is the refractive index of the skin, would be reflected back into the tissue. Typically, the critical angle for the air-skin interface is 41.8° (based on a refractive index of 1.5). The angle of incidence of the excitation source 12 and detector 28 may also be varied to obtain optimal optical properties.

In another embodiment of the invention, the angle of incidence of the excitation (i. e. the angular orientation of the excitation source 12) could be varied during the course of the measuring procedure to measure the time-resolved bidirectional fluorescence, reflectance, and/or transmittance. Similarly, the detector 28 orientation may be varied for collecting the fluorescence and reflectance signals at different angles. Alternatively, several liquid guides or fiber optics transporting the excitation pulse or the directional fluorescence, reflectance, and or transmittance signals could be installed at fixed angles.

The received energies from the detector 28 are then processed by the processing unit and computer software 36. The processing unit may comprise a computer, as shown in FIG. 1, or a small hand-held, portable device. In a preferred embodiment, the modified method of characteristics may be used in an algorithm to process the incoming signal from the detector, as described in further detail below. Because different fluorophores have different lifetimes, the time resolved approach of the present invention is capable of discriminating among fluorophores (that otherwise could not be distinguished using steady-state measurements).

The isolation of the individual fluorophores is preferably achieved through deconvolution of the transient signal, a process described in more detail in (O'Connor, D. V. and D. Phillips, 1984. *Time-correlated Single Photon Counting.* Academic Press, London), herein incorporated by reference in its entirety. The data may be processed using commercial software such as Fluofit™ by PicoQuant GmBH to recover the skin fluorophores' lifetimes and their proportional contribution to the overall fluorescence signal from the skin. Fluorescence data may be compared and correlated with the currently available clinical laboratory values, including: subject age, glucose level, fasting blood glucose, HgA1C, and fructosamine for pre-screening and diagnosis of diabetes.

Additional information on the fluorophores locations, local concentrations, and skin morphology can be retrieved by processing the temporal signal directly provided by the detector using standard inverse techniques. The inversion consists of determining iteratively the radiation characteristics that minimize some difference between the measured and the calculated fluorescence, transmittance and/or reflectance. The calculation are performed using an algorithm, such as that for the modified method of characteristics, to solve the governing equation of electromagnetic wave transport through absorbing, scattering, and fluorescing media.

The number of excitation source elements 12 and the transmitted excitation light wavelength may be varied to alter the sensitivity of the device 10 including the analysis software. Several excitation laser diodes, light emitting diodes (LEDs), or pulsed flash lamps may be used to generate a pulse of excitation light having various wavelengths, pulse widths, repetition rate, and peak and average powers. For example, the pulse width is selected such that it is smaller than the fluorescence lifetime of the molecules or protein of interest. Since most fluorophores have more than a nanosecond lifetime, the ultra-short pulses will ideally have lengths less than a nanosecond. The frequency of the pulses may be at any rate, but is ideally at least 1 Mhz, and by be as fast as the technology permits (e.g. 40 MHz) without imposing undue cost. A range of 2.5 MHz to 40 MHz has been found to be optimal given the current state of technology. Similarly, for the frequency modulation technique, several modulation frequencies, peak and average power can be used. The excitation light may be UV, IR, visible light, or other form of electromagnetic wave commonly used in the art.

The characteristics, of the excitation light, such as wavelength, intensity, pulse frequency, pulse width, and peak power may also be varied to adjust sensitivity. As the intensity increases, the signal to noise ratio increases. However, the excitation light intensity is limited by safety criteria. For this effect, excitation source 12 deposits very little energy but can carry enough power (average power of a few microwatts) for accurate detection.

One example of a preferred excitation source 12 is the PicoQuant LED Model PLS 370. It is a class 1 laser product (LED), which requires no operator training, or any special equipment, such as eye protection, to operate the device. It is also safe to expose the human body to the non-ionizing radiation from this device. Moreover, the peak power of the device is 2.5 mW and average power of 5 µW at a 2.5 MHz repetition rate. The surface area of skin exposed to the excitation source is 2 cm in diameter or approximately 3.14 cm2. Consequently, the excitation source presents minimal risk to the patient.

The optometric device 10 is preferably configured to be used on the patient's forearms, feet, earlobes, and hands. However, it may be used on any region on the patient's body that is readily accessible and appropriate light absorption characteristics.

Figure 4:
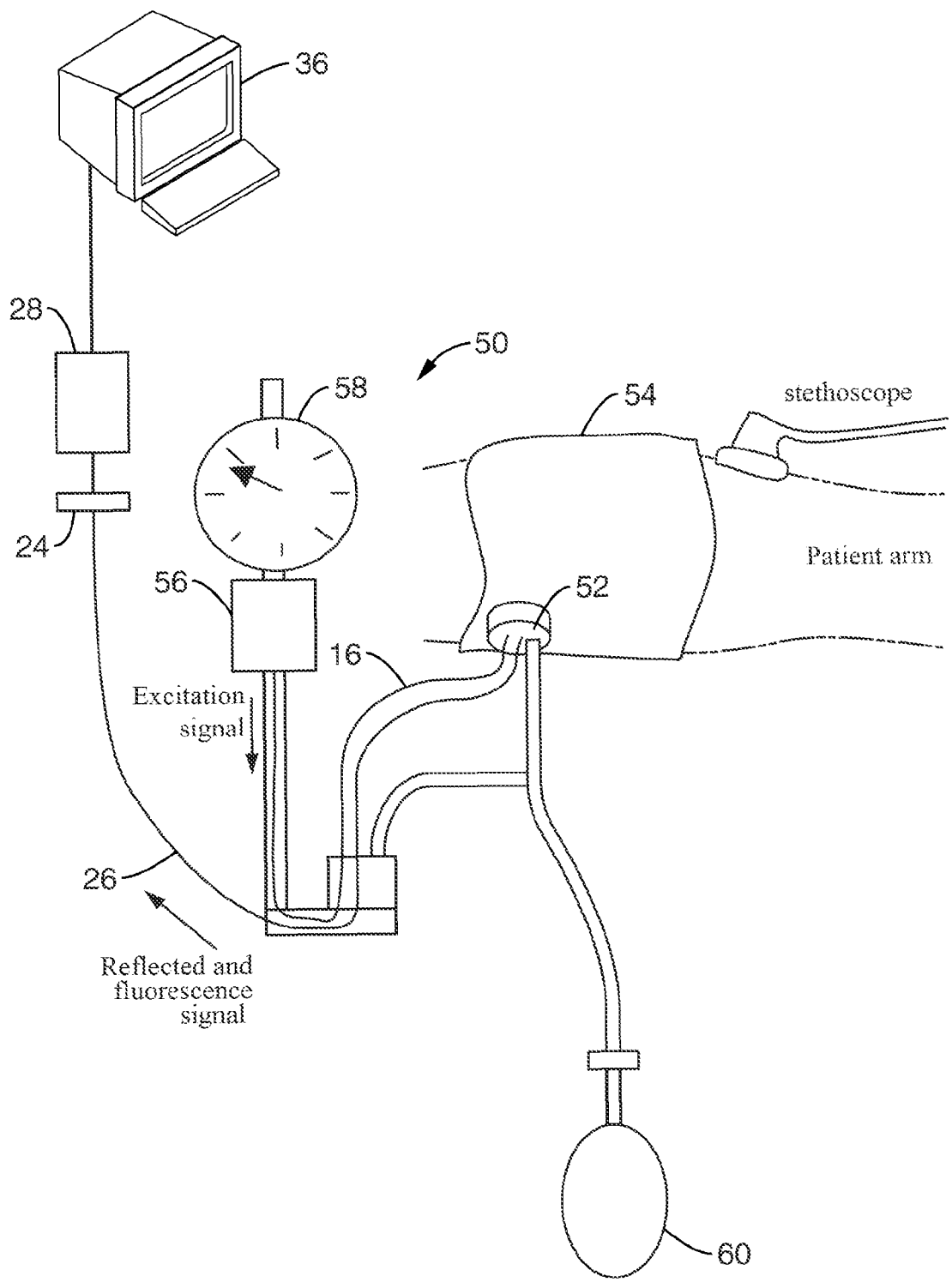
FIG. 4 illustrates a diabetes pre-screening device and blood pressure monitor in accordance with the present invention.

FIG. 4 illustrates an optometric device 50 integrated with a blood pressure monitoring system, wherein a system of fiber optic heads or light guides connected to one or more light sources and detector(s) will be placed at different locations on the forearm. This configuration has the added advantage that blood circulation is reduced in the forearm, thus limiting the absorption of the excitation light by blood. In addition, the numerous patients that have their blood pressure checked at each physician visit could have their fluorescence signal taken simultaneously. This would allow for universal screening, early detection and reduced complications of diabetes The optometric device 50 has a light guide 52 coupled to sphygmomanometer cuff 54 to be placed on the patient's arm. An excitation source 56, comprising a driver and one or more pulsed sources (e.g. LEDs), may be coupled to a manometer 58 commonly used in blood pressure monitoring devices. While pressure is applied to the patient's arm via the sphygmomanometer cuff 54 and inflation bulb 60, an excitation signal 16 from the from the pulsed-source is sent to the light guide unit 52. The reflected and fluorescence signal 26 is then received by the detector for processing by computer 36.

Figure 5:
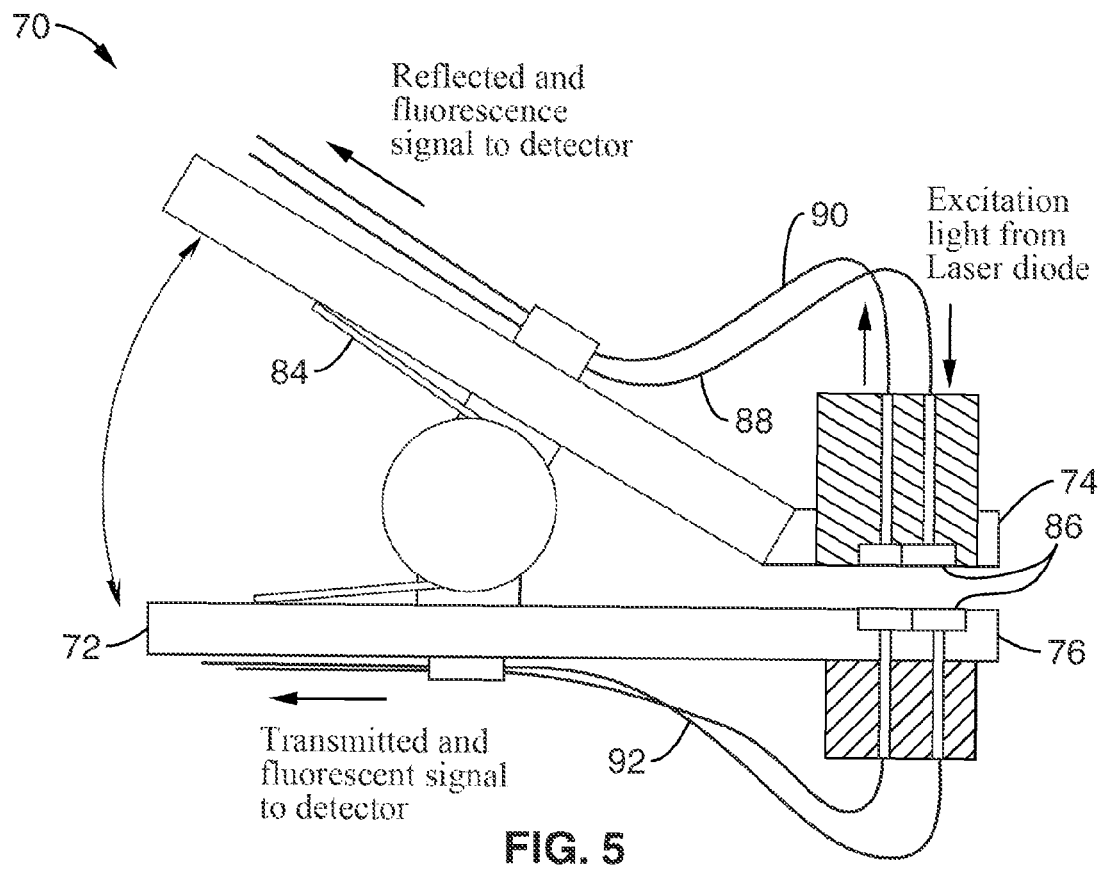
FIG. 5 illustrates a clip on time-resolved fluorescence optometric device in accordance with the present invention.
Figure 6:
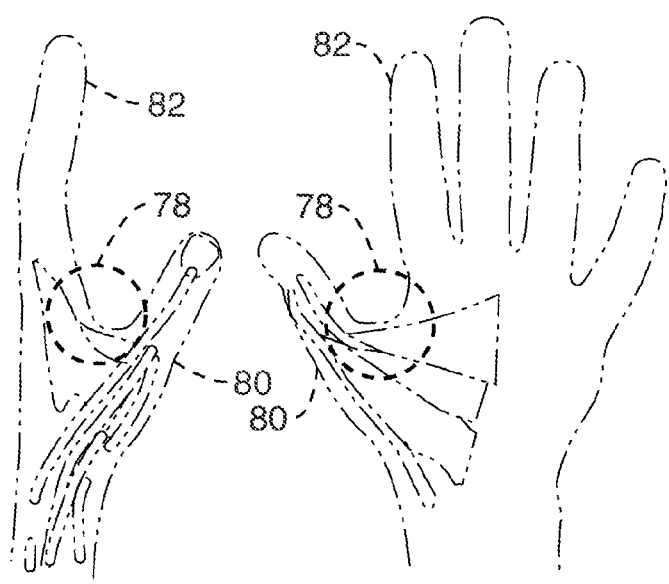
FIG. 6 illustrates exemplary skin target locations for the device shown in FIG. 5.

FIG. 5 illustrates another alternative embodiment comprising a clip-on optometric device 70. The clip-on optometric device 70 is configured to be positioned on opposing sides of the skin flap 78 between the thumb 80 and forefinger 82, as shown in FIG. 6. Alternatively, the clip on device 70 may be used on the patient's earlobes. In this region, blood vessels and fat are fairly limited and only skin is present. It also offers larger surface area for adequate optical contact between the non-invasive device 70 and the skin 80. Other possible sensing areas include the tongue and lips of the patient.

Moreover, the skin flap 78 and all of the above-mentioned sensing locations offer alternative tactics by enabling simultaneous time-resolved fluorescence, reflectance, and transmittance measurements from both faces of the skin flap 78. As seen in FIG. 5, the device 70 comprises two opposing optical sensor heads: upper head 74 and lower head 76. The upper and lower heads 74, 76 are configured to be positioned on opposing sides of skin flap 78, and pressure may be applied to the skin flap 78 via spring 84 to ensure proper optical contact. Each sensor head may have one or more light guides 86 for directing and transmitting optical signals. For example, upper head 74 may have fiber optics or light guides for directing excitation light 88 from a diode, and for transporting the reflected and fluorescence signal 90 to the detector. Correspondingly, the lower head 76 may have a light guide for directing the transmitted and fluorescence signal to the detector. In either case, one or more monochromators or filters may be used to separate the transmitted from the fluorescence signal and reflected from the fluorescence signal.

In one embodiment, the light guides may also be translationally and angularly oriented with respect to each other to vary the light path traveled through the skin. For example, the detector light guides may be oriented off normal, and away from the excitation source light guides. The light guides and/or heads may be motorized to vary angle or position, or, an array of light guides may be positioned on the head at different locations and orientations, thus capable of retrieving a number of data points corresponding to the different locations or orientations.

The angular profile of the reflectance and the fluorescence signals may be valuable in obtaining data for a number of biomedical applications. In addition, biological or morphological changes of the human skin caused by aging or diseases could also affect the directional reflectance and fluorescence signals by changing the scattering phase function and refractive index of the skin layers.

The additional measurements afforded by the optometric device 70 enable retrieval of the morphological properties of the skin thickness and optical properties of each layer, which are also affected by some diseases, e.g. diabetes as previously discussed.

The time-resolved fluorescence, reflectance, and transmittance data received from each patient may be collected and stored in a confidential database. This data may not only be used to validate the optical model and the simulations performed, but also develop a baseline of fluorescent signal for healthy subjects. In addition, for each individual, the evolution of the fluorescence signal as a function of time may be recorded at each physician visit. Deviation from the healthy patient baseline would indicate abnormal metabolic changes affecting the skin optical and fluorescence properties and the occurrence or risk of diabetes mellitus. This would allow for universal screening, early detection and reduced complications.

Statistical, error management modeling, and signal processing methods commonly used in the art may also be used to process the data. The fluorescence signal is deconvoluted in order to isolate the contribution of individual fluorophores to the apparent cumulative signal. The overall performance of the system is assessed by measuring the sensitivity of the device as a function of false negative rate.

The time-resolved fluorescence measurements in combination with the analysis software of the present invention also enable identification of the fluorophores and measurement of their location and concentration in the skin, wherein the key fluorophores correlating with known conditions are distinguished to facilitate medical diagnostics.

For example, age matched controls as the fluorescence of skin changes with age may be implemented. The fluorescence values obtained between the patients with the target condition and the age-matched controls may then be compared. Other control such as gender, race, and the like may be required depending on the disease to be detected or monitored. The control subjects will have their blood drawn for biological markers indicative of the target condition. Other laboratory testing and analysis indicative of the targeted conditions may also be used. These values are then compared with the fluorescence measurements. In addition, medical records may be used to determine when the patients were diagnosed with condition and review their clinical laboratory values.

In time-resolved fluorescence, the fluorophores are present throughout the tissue and the fluorescent light is absorbed and scattered before emerging from the tissue and reaching the detector. Thus, measurements of the fluorescent light leaving the tissue strongly depend on its optical properties. In order to capture the effects of the tissue's optical properties on the fluorescence signal and those of other parameters such as the geometry of the optical setup, an accurate model of excitation and fluorescent light transport in tissue is needed.

In order to demonstrate the capability of the method, time-dependent test problems of photons transport in biological tissues have been solved using the backward, or modified method of characteristics, which can be referenced in more detail in the following references; [1] L. Pilon and K. M. Katika, 2004. *Modified Method of Characteristics for Simulating Microscale Energy Transport*, ASME Journal of Heat Transfer, Vol. 126, pp. 735-743; [2] K. M. Katika and L. Pilon, 2005. *Modified Method of Characteristics for Solving the Transient Radiative Transfer Equation*, Invited Presentation, EUROTHERM 82, Numerical Heat Transfer 2005. Sep. 13-16, 2005, Krakow, Poland, Eds.: A. Nowak, R. A. Biaolecki; [3] K. M. Katika and L. Pilon, 2004. *Ultra-Short Pulsed Laser Transport in Turbide Media*, ASME International Meeting and Exposition, Anaheim, November, 2004, IMECE2004-59796; [4] K. M. Katika and L. Pilon, 2004.

*Backward Method of Characteristics in Radiative Transfer*, 4th International Symposium on Radiative Transfer, M. P. Menguc and N. Selguk, eds., Istanbul Turkey, Jun. 18-21, 2004, pp. 347-355; [5] K. M. Katika and L. Pilon, 2005. *Modified Method of Characteristics in Transient Radiative Transfer*, Journal of Quantitative Spectroscopy and Radiative Transfer 2005. Accepted May 10, 2005), incorporated herein by reference in their entirety. The modified method of characteristics essentially follows photons along their pathlines backward in time.

The transport of excitation and fluorescence light in skin was modeled using the steady-state radiative transfer equation (RTE) which governs light transport in absorbing, emitting and scattering media. For the excitation intensity $I_{\lambda x}$ at wavelength $I_x$ and in direction $\rho_s$, the RTE can be written as $$\frac{1}{c}\frac{\partial I_{\lambda_x}}{\partial t} + \vec{s}\cdot\nabla I_{\lambda_x} = -(\kappa_{\lambda_x} + \sigma_{\lambda_x})I_{\lambda_x} + \frac{\sigma_{\lambda_x}}{4\pi}\int\int_{4\pi} I_{\lambda_x}\Phi_{\lambda_x}(\vec{s}_i,\vec{s})d\Omega \quad (1)$$

where the light intensity, the absorption and scattering coefficients at wavelength $\lambda_x$, are denoted $I_\lambda$, $\kappa_\lambda$, and $\sigma_\lambda$, respectively. The speed of light in the medium is denoted c, while the scattering phase function $\Phi_\lambda$ represents the probability that radiation propagating in direction $\rho_{si}$ be scattered into the solid angle $d\Omega_d$ around the direction $\rho_s$. The first and second terms represent attenuation of the radiation intensity by absorption and scattering, respectively. The last term on the right hand side represents the augmentation of radiation due to in-scattering. Note that here, the emission by the medium has not been accounted for. Indeed, at the normal body temperature of 37° C., the radiation emitted by a blackbody at the excitation can safely be neglected compared to the excitation intensity. A similar equation can be written for the transport of fluorescent light, emitted by the fluorophores at wavelength $\lambda_F$ $$\frac{1}{c}\frac{\partial I_{\lambda_F}}{\partial t} + \vec{s}\cdot\nabla I_{\lambda_F} = -(\kappa_{\lambda_F} + \sigma_{\lambda_F})I_{\lambda_F} + \frac{\sigma_{\lambda_F}}{4\pi}\int\int_{4\pi} I_{\lambda_F}\Phi_{\lambda_F}(\vec{s}_i,\vec{s})d\Omega_i + \frac{QY_{\lambda_x}}{4\pi\tau}\kappa_{\lambda_F}\int_0^t \exp\left[-\frac{(t-t')}{\tau}\right]G(t')dt' \quad (2)$$

The last term in Equation (2) represents fluorescence emission due to the excitation light and G(t') is the distribution of incident light in the medium and is defined as $$\int\int_{4\pi} I_{\lambda_F}d\Omega'.QY_{\lambda_x}$$

is the quantum yield of the fluorophores and $\kappa_{\lambda xF}$ is the absorption coefficient at the excitation wavelength and $\tau$ denotes the lifetime of the fluorophores where the light intensity, the absorption and scattering coefficients at wavelength $\lambda$, are denoted $I_\lambda$, $\kappa_\lambda$, and $\sigma_\lambda$, respectively. The speed of light in the medium is denoted c, while the spectral intensity of blackbody radiation is $I_{b\lambda}$ and $\Phi_\lambda$ is the scattering phase function. The first term on the right-hand side of Equation (1) accounts for the attenuation of light due to absorption and out-scattering within the medium. The second term corresponds to the light emitted by the medium. It is neglected at the excitation wavelength and depends on the quantum yield and lifetime at the emission wavelength. The last term accounts for augmentation of the intensity due to in-scattering coming from all directions. Equation (1) is valid for both the excitation light and the autofluorescence traveling through and emitted by the skin.

Figure 7:
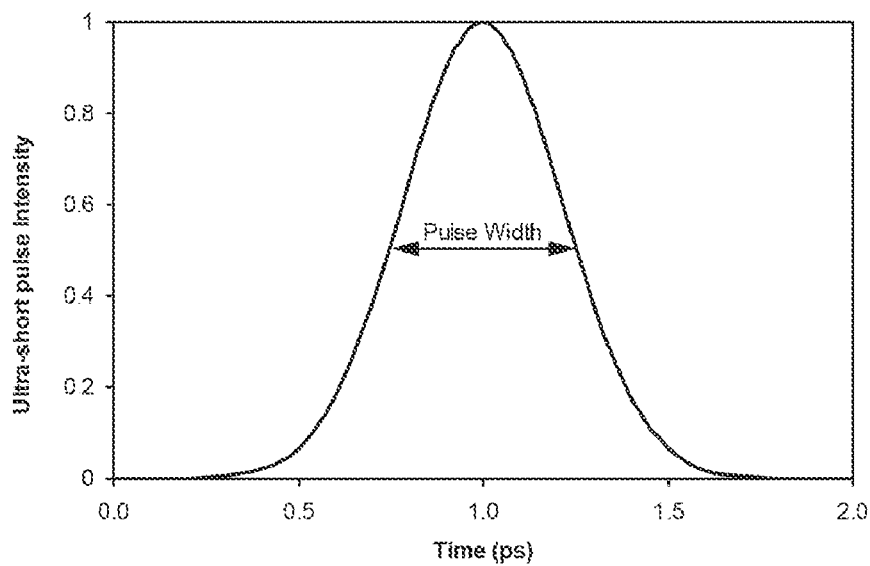
FIG. 7 is graph of an exemplary ultra-short excitation pulse intensity over time.
Figure 8:
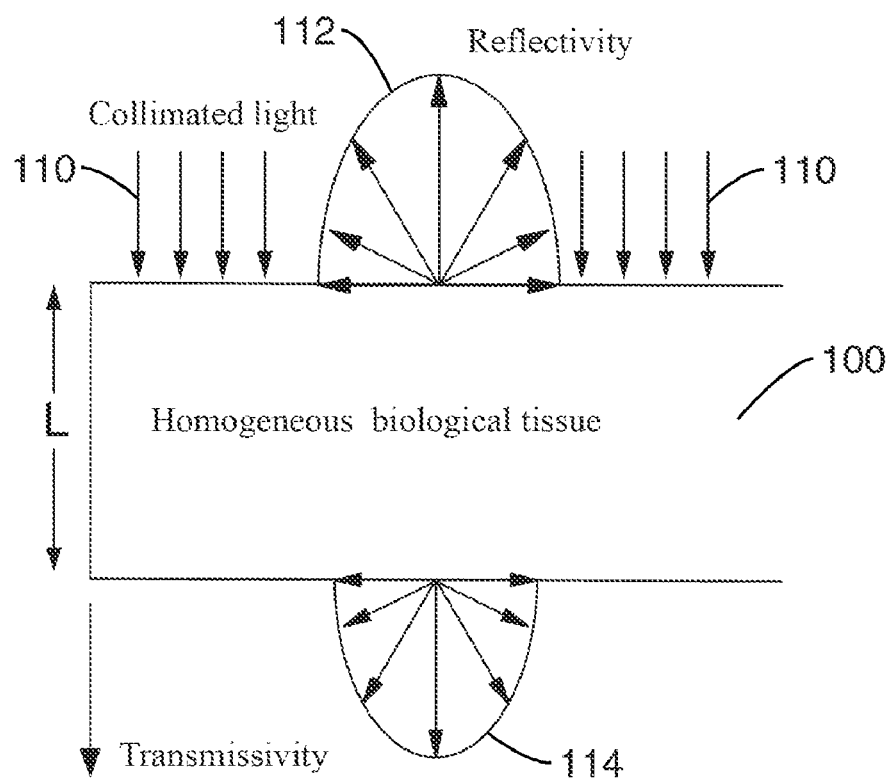
FIG. 8 is a schematic view of a Gaussian ultra short laser pulse incident on a simulated slab of tissue.

Referring to FIG. 8, a one-dimensional thick slab 100 of biological tissues subjected to an incident collimated Gaussian ultra-short laser pulse 110 of intensity I(t) is governed by the equation:

$$I(t) = I_0\exp\left[-4\ln2\left(\frac{t}{t_p}-3\right)^2\right]$$

where $t_p$ is the pulse width as shown in FIG. 7. As shown in FIG. 8, the laser pulse 110 results in reflectivity 112 and transmissivity 114. The tissue is assumed to have a typical absorption coefficient of 6 mm$^{-1}$, and a scattering coefficient of 0.012 mm$^{-1}$. The pulse is such that $t_p$ equals 1 picoseconds. The scattering phase function $\Phi$ is assumed to be the Henyey-Greenstein function:

$$\Phi = (1-g^2)/(1+g^2-2g\cos\theta)^{3/2}$$

with a constant asymmetric factor equal to g =0.835 and corresponding to a strongly forward scattering medium.

The full radiative transfer Equation (1) is solved for simulating ultra-short pulse laser transport in tissues, disregarding the diffusion approximation.

The results are a unconditionally stable, very accurate, and fast numerical method for time-dependent light transport in biological tissues.

The modified method of characteristics proposed in [Katica and Pilon (2004a, b, c)] is used to solve the three-dimensional time-dependent light transport equation in biological tissues. It consists of transforming the partial differential Equation (1) into an ordinary differential equation solved along the pathline of the photons.

The conventional implementation (or direct marching method) of the method of characteristics is based on the Lagrangian formulation: the photons are identified and located at initial time t=$t_0$ and followed at subsequent time as they are transported. In three-dimensional photon transport, however, the deformation that the initial mesh undergoes as time progresses leads to deterioration of the numerical solution.

Figure 9:
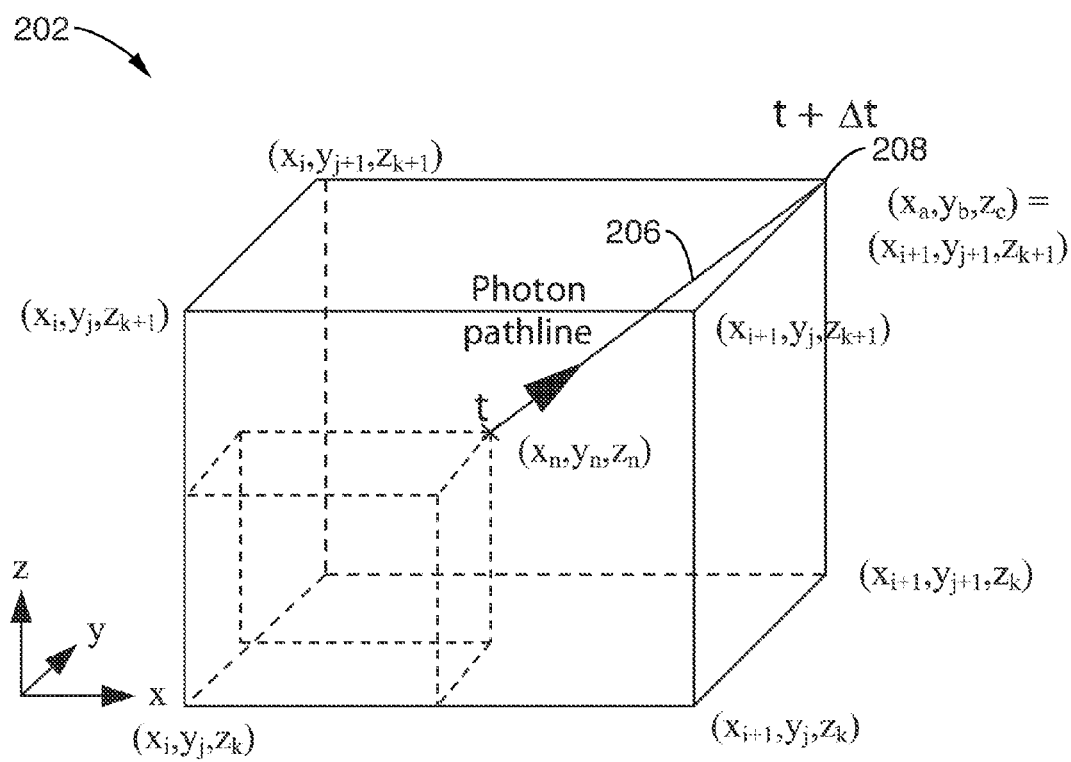
FIG. 9 is an illustration of a typical computational cell containing the path-line of heat carriers.

Referring now to FIG. 9, the modified method of characteristics or (inverse marching method) is an interpretation of the Lagrangian approach that overcomes the difficulties related to mesh deformation. Based on a pre-specified grid 202 shown in FIG. 9, the backward method of characteristics follows the photons 206 backward in time from their endpoint 208 at time t+$\Delta$t, to the excitation source 104 at time t (as opposed to forward from the excitation source in the case of direct marching method).

In Cartesian coordinates, the total time derivative of the spectral intensity $I_\lambda = I_\lambda(x, y, z, t)$ with respect to time t in the direction $(\theta,\phi)$ can be written as $$\frac{DI_\lambda}{Dt} = \frac{\partial I_\lambda}{\partial t} + \frac{\partial I_\lambda}{\partial x}\frac{dx}{dt} + \frac{\partial I_\lambda}{\partial y}\frac{dy}{dt} + \frac{\partial I_\lambda}{\partial z}\frac{dz}{dt}$$

We further define the photon characteristic path-lines 206 as dx/dt=c·sin θ cos φ,
dy/dt=c·sin θ sin φ, and
dz/dt=c·cos θ.

Then, along the characteristic curves in the (x, y, z, t) space, Equation (1) can be written as $$\frac{DI_\lambda}{Dt} = -(\kappa_\lambda + \sigma_\lambda)I_\lambda + \kappa_\lambda I_{b,\lambda} + \frac{\sigma_\lambda}{4\pi}\int_{4\pi} I_\lambda \Phi_\lambda d\Omega$$

where $DI_\lambda/Dt$ denotes the substantial derivative of $I_\lambda$, i.e., the total time derivative along the path-line 206 of the photons. Unlike the few other methods currently being developed (essentially reverse Monte-Carlo) the modified method of characteristics is (i) fast, (ii) unconditionally stable, (iii) very accurate, and (iv) multidimensional.

The modified method of characteristics will be used to determine the local scattering and absorption properties of the tissue given the refractive index of the medium (typically 1.4 for tissues). Given the speed of light in the medium, the depth of light penetration in the tissue can be calculated at any instant of time t. The reflectance at time t is dependent only on the properties of this volume of tissue. At t =Δt, the reflectance is measured and the depth to which light has penetrated is cΔt. Assuming that the properties of tissue have not varied over this depth, the optical properties of the tissue till this depth can be computed using any of the standard techniques used in inverse computations with reflectance as the input parameter.

Next, the time step is advanced and the reflectance is measured and the incremental depth of light penetration is computed. The properties of this incremental depth are computed based on the knowledge of the properties of the medium up to this depth and knowledge of the reflectance at this time step. The procedure is continued till the properties of the medium are known at every location. This procedure is used to recover the spatial variation of the absorption and scattering properties of layered media ranging from skin to thin films.

Mathematical analysis of the time-resolved signal can also give information about the morphology and physiology of the skin. Indeed, the reflectance, transmittance, and fluorescence signals feature maxima, minima, scups, and inflection points that provide additional information about the skin structure.

Figure 10:
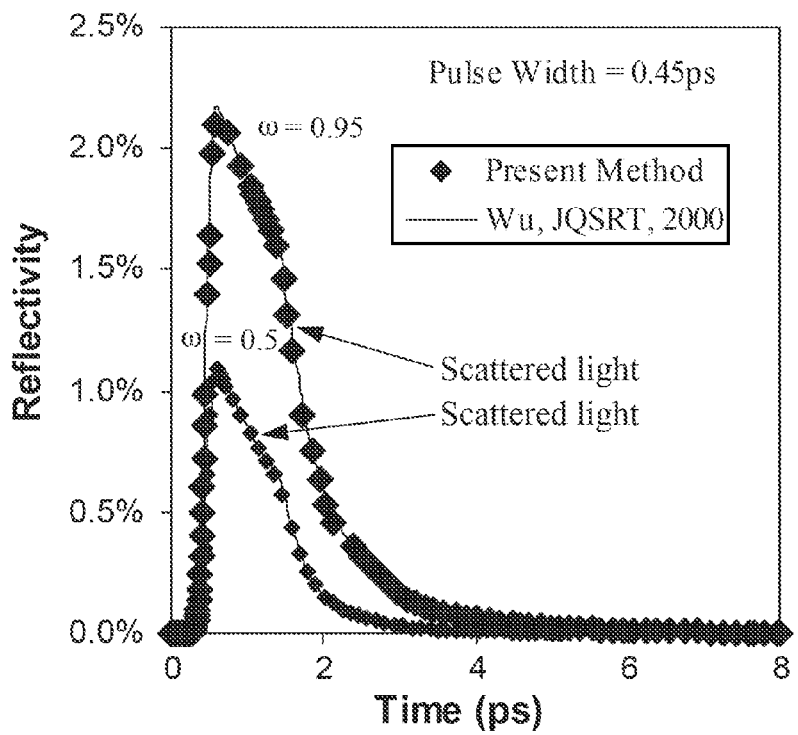
FIG. 10 is a graph of transient reflectivity of simulated homogenous biological tissues over time.
Figure 11:
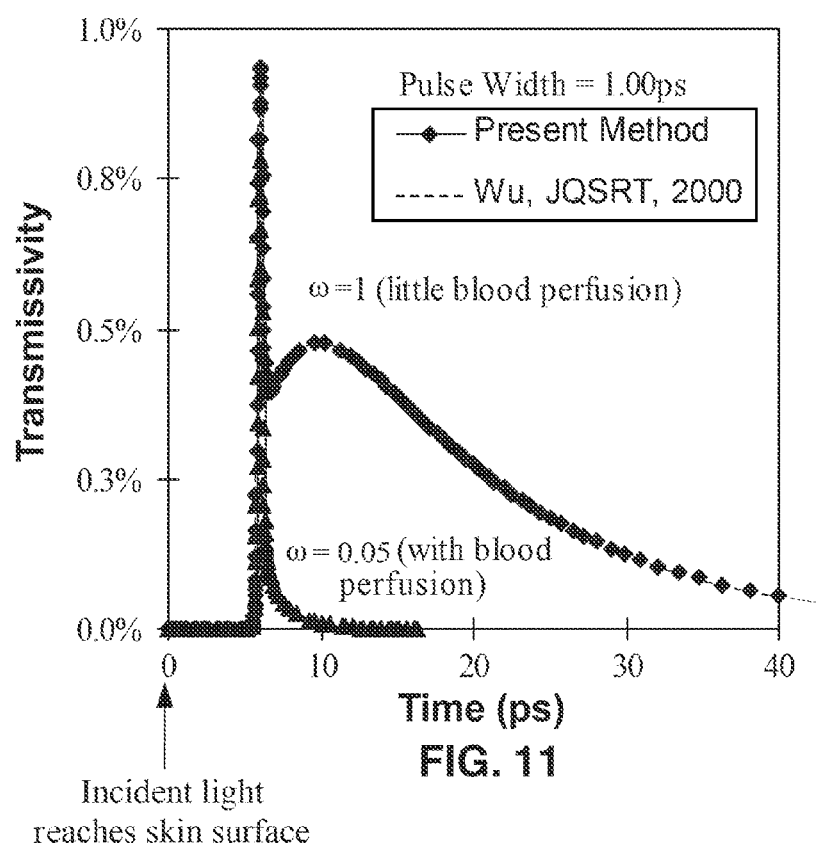
FIG. 11 is a graph of transient transmissivity of simulated homogenous biological tissues over time.

FIGS. 10 and 11 show the hemispherical transmittance and reflectance as a function of time computed by integrating the directional transmitted intensity over the lower hemisphere, where $$[\omega = \sigma/(\sigma+\kappa)].$$

Two peaks can be observed. The first peak corresponds to the light directly transmitted or reflected by the tissue in the normal direction. Then a second intensity peak is observed caused by the scattered photons emerging out of the tissue.

Figure 12:
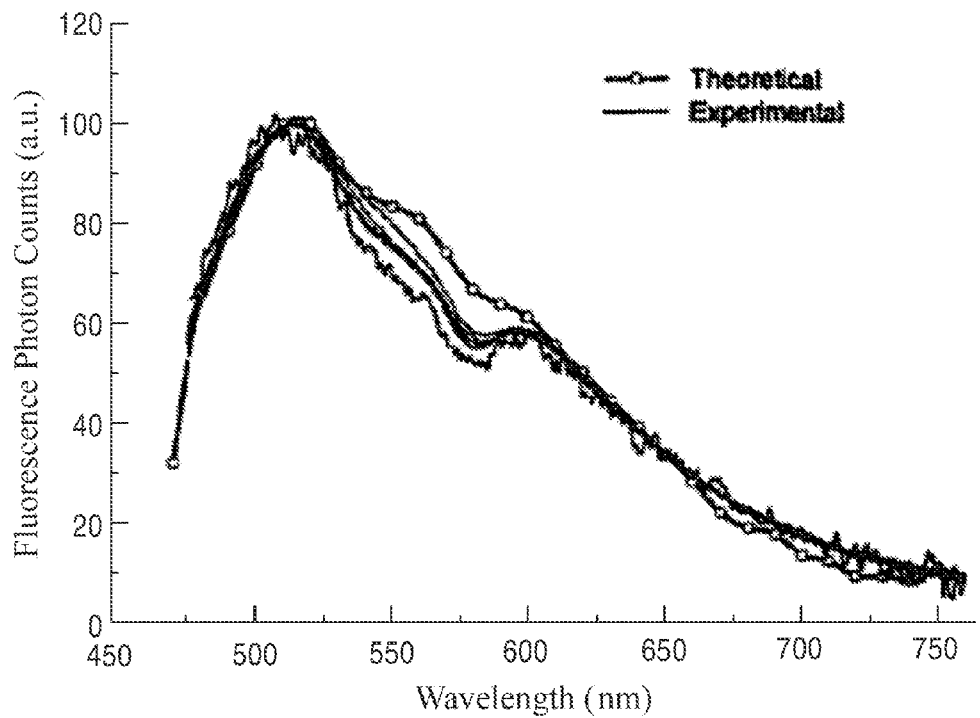
FIG. 12 is a graph illustrating the comparison of reconstructed skin autofluorescence measurements with experimental in-vivo data.

FIG. 12 compares numerical results for the reconstructed skin autofluorescence spectrum curve of the skin model reported in Table 1 (as reported by Zeng et al., 1997) and in-vivo measurements of steady-state autofluorescence of skin for Caucasian and Asian patients. Very good agreement is observed, confirming the validity of the skin optical model.

Figure 13:
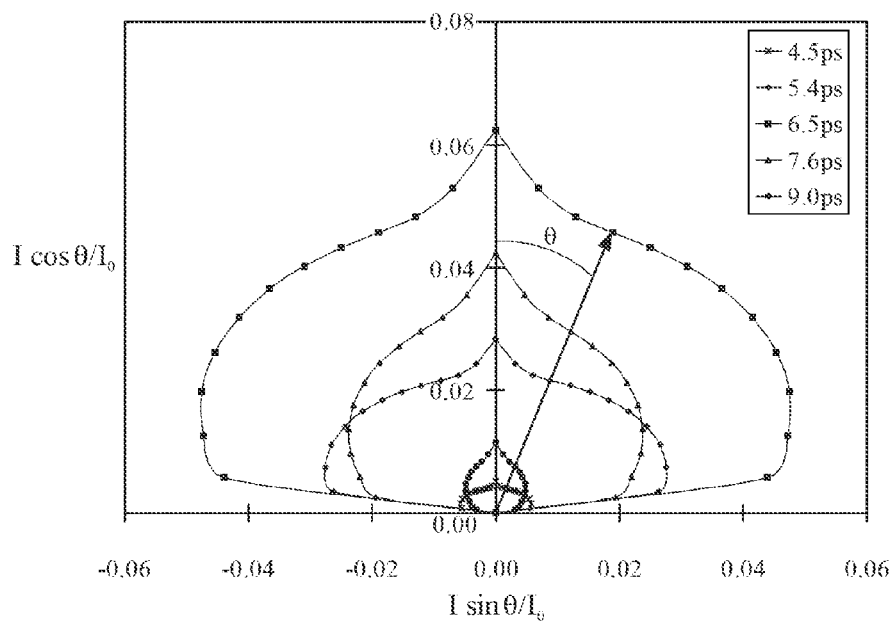
FIG. 13 illustrates a simulation in accordance with the methods of the present invention predicting the directional reflectance of the skin model of FIG. 12 exposed to an ultra-short pulse collimated laser beam at wavelength λ of 442 nm and pulse width of 2 ps.
Figure 14:
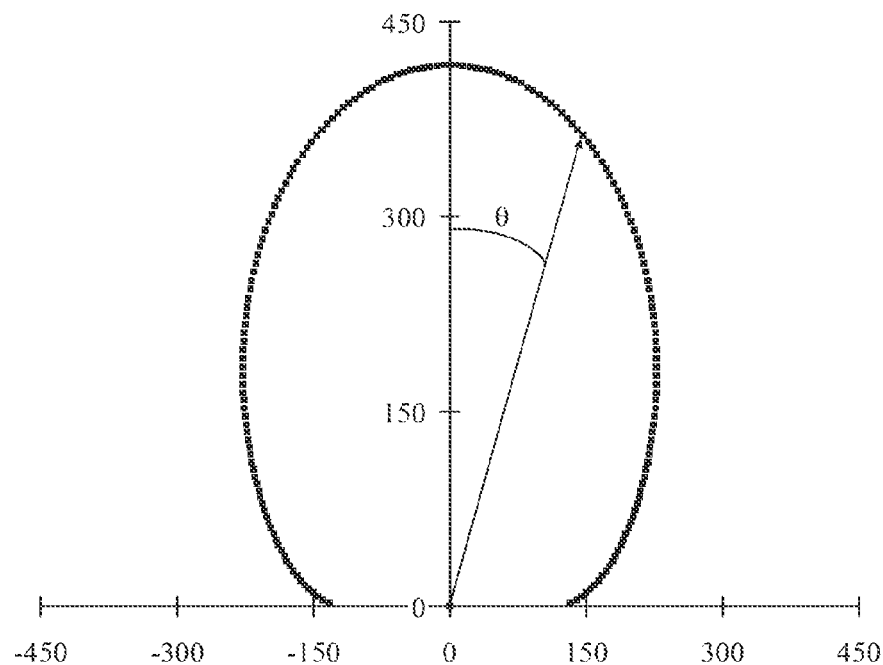
FIG. 14 shows another simulation predicting the directional steady-state fluorescence of the skin model of FIG. 12 exposed to a collimated laser beam at excitation wavelength 442 nm and emission of 520 nm, respectively.

FIG. 13 shows results from a simulation in accordance with the methods of the present invention predicting the directional reflectance of the abovementioned skin model exposed to an ultra-short pulse collimated laser beam at wavelength λ of 442 nm and pulse width of 2 ps. FIG. 14 shows another simulation predicting the directional steady-state fluorescence of the above mentioned skin model exposed to a collimated laser beam at excitation wavelength 442 nm and emission of 520 nm, respectively.

Figure 15:
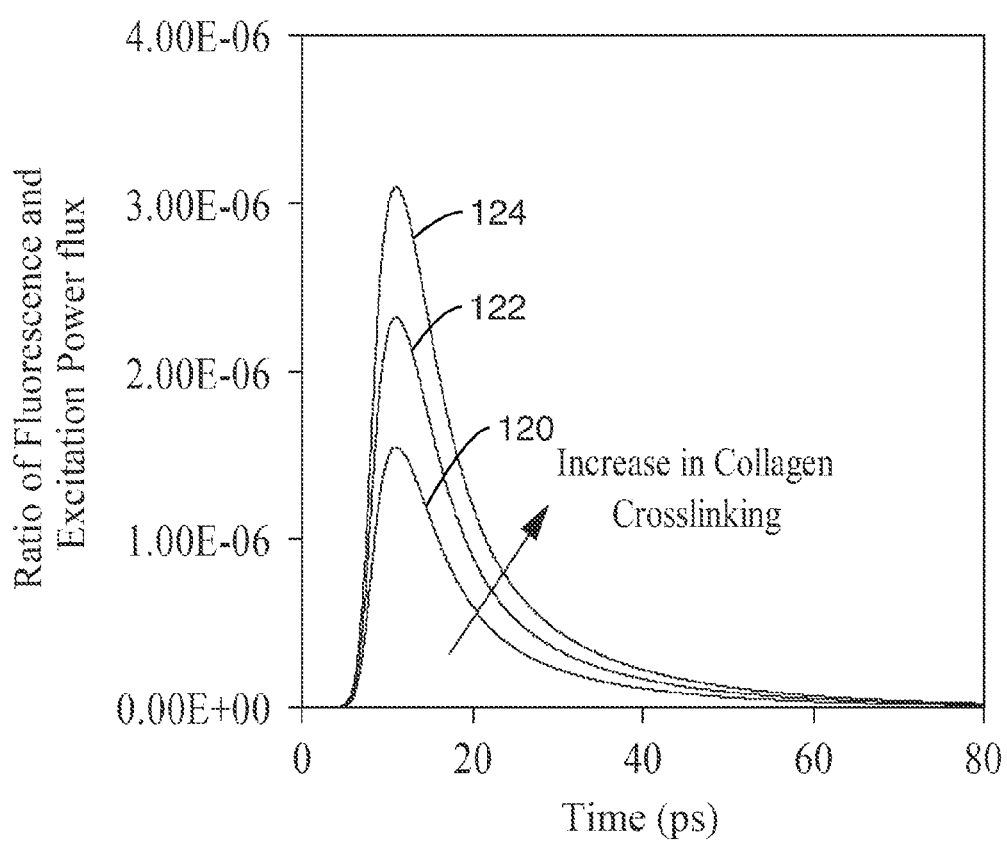
FIG. 15 shows the simulated time-resolved fluorescent signal of skin from collagen with different concentrations of fluorophores.

FIG. 15 shows the simulated time-resolved fluorescent signal of skin from collagen with different concentrations of fluorophores. Line 120 corresponds to healthy subjects, line 122 corresponds to patients having fluorophore concentration of 50%, and line 124 corresponds to concentrations 100% larger than normal. The time decay of cross-linked collagen and elastin are 2.7 ns centered at 440 nm and 2 ns centered at 500 nm. Both proteins are present in the skin mainly in the dermis. One can see that even with the scattering caused by the multiple skin layers, the skin autofluorescence is highly sensitive to fluorophore concentration.

Moreover, the energy emitted by a commercial typical laser diode with 100 ps pulse width at around 400 nm ranges from 10 mJ to 100 mJ. Then, the fluorescence signal should have energy of the order of 10 nJ to 100 nJ which can be detected by a standard photomultiplier tube (PMT) (e.g., the Hamamatsu H5783). The incident and fluorescent energy per unit surface area may be concentrated by using lenses connected to fiber optics.

A time-resolved fluorescence skin model may also be created that accounts for the absorption and fluorescence of collagen, elastin, and other fluorophores accumulated in the skin to analyze the time-resolved fluorescence spectra. A reliable skin model may be developed by combining (i) the numerical tool described above for ultra-short pulse light transport in multilayered turbid media, and (ii) optical and fluorescent characteristics of skin and its constituents reported in the literature across the UV and visible spectrum.

The optical skin model to be developed will account for (1) absorption by endogenous chromophores at the excitation and emission wavelengths which depend on skin complexion and patient's age, (2) autofluorescence by natural skin constituents, and (3) absorption and emission by accumulated fluorophores. Time-resolved fluorescence characteristics include (i) lifetime, (ii) quantum yield, and (iii) excitation and emission wavelengths.

In an alternative embodiment, an optical model may be used accounting for more complex skin morphology. Instead of treating the skin as a series of plane parallel layers, the exact skin morphology will be obtained using an image analysis software and a microphotograph of a cross-section of human skin. The optical properties ($\kappa_\lambda$, $\sigma_\lambda$, 101 $_\lambda$, and fluorescence characteristics) of human skin will be measured following the procedure available in (Baillis et al., 2004a, b). The Monte Carlo method may also be used instead of the modified method of characteristics, as it can simulate complex geometries and configurations and capture real physical conditions. The source code is readily available online (Jacques, 1998)

The method of the present invention has the following advantages: (1) non-invasive, (2) low cost, (3) allows for the motion of the subject thus making possible the study of infant, children, elderly, and patient with severe movement disorder, (4) uses non-ionizing radiation and therefore has no limits on the number of scans or pulses, (5) does not require fasting, (6) enables the determination of the location and concentration of fluorophores in the skin due to time-resolution. These pieces of information combined with lifetime measurement enable (7) the ability to distinguish between fluorophores. In addition, measurements are (8) not affected by skin conditions (tan, hair, or pigmentation) as much as steady-state fluorescence measurements (Fang et al., 2004), and (9) the device is easy to operate in clinical settings allowing for measurements to be done routinely by health professionals such as nurses at all physician visits or at least annually.

Although the description above contains many details, these should not be construed as limiting the scope of the invention but as merely providing illustrations of some of the presently preferred embodiments of this invention.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Optical properties of the seven layer skin model (Zeng et al., 1997)

| | | $\lambda$ = 442 nm (excitation) | | | | $\lambda$ = 520 nm (fluorescence) | | |
|---|---|---|---|---|---|---|---|---|
| Layer | thickness μm | n | $\sigma_s$ (cm$^{-1}$) | $\kappa$ (cm$^{-1}$) | g | n | $\sigma_s$ (cm$^{-1}$) | $\kappa$ (cm$^{-1}$) | g |
| Air | | 1.0 | | | | 1.0 | | | |
| Stratum corneum | 10 | 1.45 | 190 | 2300 | 0.9 | 1.45 | 40 | 570 | 0.77 |
| Epidermis | 80 | 1.4 | 56 | 570 | 0.75 | 1.4 | 40 | 570 | 0.77 |
| Papillary dermis | 100 | 1.4 | 6.7 | 700 | 0.75 | 1.4 | 5 | 500 | 0.77 |
| Upper blood plexus | 80 | 1.39 | 67 | 680 | 0.77 | 1.39 | 24.5 | 500 | 0.79 |
| Reticular dermis | 1500 | 1.4 | 6.7 | 700 | 0.75 | 1.4 | 5 | 500 | 0.77 |
| Deep blood plexus | 70 | 1.34 | 541 | 520 | 0.96 | 1.34 | 181 | 500 | 0.96 |
| dermis | 160 | 1.4 | 6.7 | 700 | 0.75 | 1.4 | 5 | 500 | 0.77 |
| Subcutaneous fat | | 1.46 | | | | 1.46 | | | |

What is claimed is:

1. A method for non-invasively probing the inner structure of the skin of a patient, comprising:
   directing an excitation pulse at a region of the patient's skin;
   exciting a portion of the patient's skin as a result of the excitation pulse at the region to generate a fluorescence signal indicative of the composition of the patient's skin;
   detecting the fluorescence signal generated by the excitation pulse;
   measuring an intensity decay of the fluorescence signal as a function of time to detect development of a metabolic disease affecting the patient;
   measuring the reflectance of the excitation pulse;
   measuring the transmittance of the excitation pulse; and
   wherein the transmittance, reflectance, and time-resolved fluorescence measurements are performed simultaneously;
   wherein the transmittance, reflectance, and time-resolved fluorescence measurements are calculated using an inverse marching method.

2. A method as recited in claim 1, wherein directing an excitation pulse comprises repeatedly directing a plurality of excitation pulses in succession at the region of the patient's skin.

3. A method as recited in claim 2, wherein measuring the fluorescence signal comprises applying the modified method of characteristics to calculate fluorescence transport within the patient's skin.

4. A method as recited in claim 2, wherein the successive pulses are added to increase the signal-to noise ratio of the signal.

5. A method as recited in claim 2:
   wherein the fluorescence signal comprises intensity decay values of fluorophores of one or more molecules or proteins; and
   wherein the plurality of excitation pulses each have a pulse width that it is smaller than the fluorescence lifetime of the fluorophores.

6. A method as recited in claim 1, further comprising:
   storing fluorescence decay values acquired from a plurality of reference patients in a database.

7. A method as recited in claim 6, further comprising:
   comparing the measured fluorescence signal to the stored fluorescence decay values.

8. A method as recited in claim 7, further comprising:
   using the compared fluorescence signal to monitor the long-term effect of cholesterol in the patient.

9. A method as recited in claim 7, further comprising:
   using the compared fluorescence signal to monitor genetic changes in the patient.

10. A method as recited in claim 1, further comprising identifying one or more fluorophores from the measured fluorescence signal, the one or more fluorophores corresponding to one or more measured intensity decay values.

11. A method as recited in claim 10, further comprising locating one or more fluorophores within the region of skin.

12. A method as recited in claim 10, wherein the fluorescence signal is deconvoluted to isolate the contribution of individual fluorophores to a cumulative signal.

13. A method for non-invasively probing the inner structure of the skin of a patient, comprising:
   directing an excitation pulse at a region of the patient's skin;
   exciting a portion of the patient's skin as a result of the excitation pulse at the region to generate a fluorescence signal indicative of the composition of the patient's skin;
   detecting the fluorescence signal generated by the excitation pulse;
   measuring an intensity decay of the fluorescence signal as a function of time to detect development of a metabolic disease affecting the patient;
   measuring the reflectance of the excitation pulse;
   measuring the transmittance of the excitation pulse;

wherein the transmittance, reflectance, and time-resolved fluorescence measurements are performed simultaneously; and wherein the transmittance, reflectance, and time-resolved fluorescence measurements are calculated by approximating photon paths from the detector to the source of the photons.

14. A method as recited in claim 13, wherein directing an excitation pulse comprises repeatedly directing a plurality of excitation pulses in succession at the region of the patient's skin.

15. A method as recited in claim 14, wherein measuring the fluorescence signal comprises applying the modified method of characteristics to calculate fluorescence transport within the patient's skin.

16. A method as recited in claim 14, wherein the successive pulses are added to increase the signal-to noise ratio of the signal.

17. A method as recited in claim 14, further comprising identifying one or more fluorophores from the measured fluorescence signal.

18. A method as recited in claim 17, further comprising locating one or more fluorophores within the region of skin.

19. A method as recited in claim 17, wherein the fluorescence signal is deconvoluted to isolate the contribution of individual fluorophores to a cumulative signal.

20. A method as recited in claim 13, further comprising:
storing fluorescence signal values acquired from a plurality of reference patients in a database.

21. A method as recited in claim 20, further comprising:
comparing the measured fluorescence signal to the stored fluorescence signal values.

22. A method as recited in claim 21, wherein the compared fluorescence signal is used to monitor the long-term effect of cholesterol in the patient.

23. A method as recited in claim 21, wherein the compared fluorescence signal is used to monitor genetic changes in the patient.

* * * * *